United States Patent
Bernard (10) Patent No.: US 8,984,944 B2
(45) Date of Patent: Mar. 24, 2015

(54) METHOD AND SYSTEM FOR DIAGNOSIS OF THE INTERNAL STATE OF A BATTERY THROUGH ACOUSTIC EMISSION

(71) Applicant: IFP Energies Nouvelles, Rueil-Malmaison Cedex (FR)

(72) Inventor: Julien Bernard, Oullins (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 317 days.

(21) Appl. No.: 13/623,333

(22) Filed: Sep. 20, 2012

(65) Prior Publication Data
US 2013/0091950 A1   Apr. 18, 2013

(30) Foreign Application Priority Data
Sep. 30, 2011   (FR) ...................... 11 02983

(51) Int. Cl.
| | | |
|---|---|---|
| G01N 29/14 | (2006.01) | |
| G01R 31/36 | (2006.01) | |
| H01M 10/42 | (2006.01) | |
| H01M 10/48 | (2006.01) | |

(52) U.S. Cl.
CPC ............ *G01N 29/14* (2013.01); *G01R 31/3606* (2013.01); *H01M 10/4207* (2013.01); *H01M 10/4285* (2013.01); *H01M 10/482* (2013.01); *G01R 31/3679* (2013.01)
USPC .................................. 73/587; 73/602; 73/801

(58) Field of Classification Search
USPC ................ 73/587, 600, 645, 788, 801, 804
See application file for complete search history.

(56) References Cited

U.S. PATENT DOCUMENTS

| | | | |
|---|---|---|---|
| 4,884,449 A * | 12/1989 | Nishimoto et al. ............. 73/660 |
| 5,533,413 A * | 7/1996 | Kobayashi et al. .......... 73/865.9 |
| 6,037,777 A | 3/2000 | Champlin | |
| 6,144,188 A | 11/2000 | Okada et al. | |
| 6,332,362 B1 * | 12/2001 | Lee et al. ........................ 73/659 |
| 6,778,913 B2 | 8/2004 | Tinnemeyer | |
| 8,723,673 B2 * | 5/2014 | Meiksin et al. ............... 340/566 |
| 2007/0090843 A1 | 4/2007 | De Doncker et al. | |
| 2012/0090402 A1 | 4/2012 | Hojo | |

FOREIGN PATENT DOCUMENTS

| | | |
|---|---|---|
| DE | 10 2009 018 079 A1 | 10/2010 |
| EP | 0 957 560 A2 | 11/1999 |
| EP | 0 880 710 B1 | 8/2004 |
| FR | 2 874 701 A1 | 3/2006 |
| FR | 2 949 908 | 3/2011 |
| FR | 2 956 486 A1 | 8/2011 |
| JP | 7-6795 | 1/1995 |
| JP | 2010071945 * | 4/2010 |
| JP | 2012042440 * | 8/2010 |
| WO | WO 2006/024802 A1 | 3/2006 |
| WO | WO 2009/036444 A2 | 3/2009 |
| WO | WO 2010/121787 A1 | 10/2010 |
| WO | WO 2011/001471 A1 | 1/2011 |
| WO | WO 2011/101553 A1 | 8/2011 |

* cited by examiner

*Primary Examiner* — J M Saint Surin
(74) *Attorney, Agent, or Firm* — Antonelli, Terry, Stout & Kraus, LLP.

(57) ABSTRACT

The invention relates to a method of estimating the internal state of a first electrochemical system for electric power storage, such as a battery, wherein at least one property relative to the internal state of the first electrochemical system is estimated from acoustic emission measurements.

39 Claims, 6 Drawing Sheets

METHOD AND SYSTEM FOR DIAGNOSIS OF THE INTERNAL STATE OF A BATTERY THROUGH ACOUSTIC EMISSION

BACKGROUND OF THE INVENTION

1. Field of the Invention

The invention relates to non-invasive diagnosis of the internal state of batteries and more particularly to the use of the acoustic emission technique for diagnosis of the internal state of batteries.

2. Description of the Prior Art

Determining the state of charge (SoC) and the state of health (SoH) of a battery is an essential criterion for characterizing the internal state of the storage elements, in order to optimize the energy discharge/charge, as well as the life of the accumulators. Knowing these criteria is all the more critical for Li-ion batteries since an ill-controlled charge for this technology can lead to thermal runaway of the cell, or even to accumulator destruction. It is therefore necessary to develop a physical measuring technique allowing characterization of the internal state, identification of defects and prognosis during service.

There are many methods of estimating the state of charge (SoC). These methods can be grouped together into three main families:

from a physical measurement by detecting a physical change in the battery following charge/discharge, for example by measuring the density of the electrolyte during discharge. This method is suitable only for stationary batteries for which the electrolyte is involved in the reaction (lead batteries for example);

from voltage, current and temperature measurements.

A first method uses coulomb-counting when the input and output current are measured and integrated in order to know the state of charge variation from a known state. This method however leads to estimation errors by disregarding phenomena such as self-discharge. Using other indicators, such as the no-load voltage or the estimation of an internal resistance as for example disclosed in U.S. Pat. No. 6,191,590 and EP Patent No. 1,835,297 A1, is also known. In this type of method, the SoC is first associated with one or more measurable or readily estimable quantities (potential, internal resistance, temperature) through the agency of static maps or of analytical functional dependencies. This type of method can in particular be used for recalibration of a coulomb-counting method during shutdown phases. However, these dependencies are in reality much more complicated than what is normally taken into account in the BMS, which often leads to SoC estimation errors. Finally, more complex methods are based on an algorithm that calculates in real time the state of charge using as input variables the "voltage-current-temperature" triptych. This alternative approach is based on mathematical battery models in order to use estimation techniques known in other fields. Patent application US-2007/0,035,307 notably describes a method of estimating the state variables and the parameters of a battery from service data (voltage U, current I, temperature T), using a mathematical battery model. The mathematical model comprises a plurality of mathematical sub-models and allows faster response. The sub-models are models of equivalent electrical circuit type, referred to as RC models, associated with restricted frequency ranges. Another SoC estimation method known in the literature ([Gu, White, etc.]) is based on the mathematical description of the reactions of an electrochemical system. The SoC is calculated from state variables of the system. This description rests on material balances, charge, energy, and on semi-empirical correlations. All these methods can be used in stationary or on-board applications, as in vehicles;

from an electric load put on the battery and in particular the electrochemical impedance spectroscopy method that uses a low-amplitude frequency load: these methods can also be used for estimating the SoH of the batteries and they are described below.

Concerning the SoH estimation methods known in the literature, in WO-2009/036,444, a reference electrode is introduced in commercial elements in order to observe the degradation reactions of the electrodes. This method however requires substantial instrumentation, notably for inserting a reference electrode inside the element, and more complex electronic management of the battery.

French Patent 2,874,701 describes a method using a temporal electric perturbation in order to compare the response obtained with a reference response. However, this method is more difficult to implement for Li-ion type elements whose response variations following this type of perturbation are very low and can therefore not allow precise SoH measurement.

SoC or SoH estimations from electrochemical impedance measurements are numerous. The simplest one uses pre-recorded charts with different states of charge and different temperatures, so as to find the state of charge from an impedance measurement, knowing the temperature. This methodology is widely used in the laboratory for determining the internal state since there are indeed changes in the impedance depending on the SoC or the SoH.

A potentially more promising method is based on the measurement, by impedance spectroscopy (EIS), of a quantity parametrized by the SoC. For example, US Published Application 2007/0,090,843 determines by EIS the frequency f± associated with the capacitive-inductive transition. A correlation between frequency f± and the SoC is presented for a lead battery, as well as for Ni—Cd and Ni-MH batteries. A similar approach is based on the modelling of the EIS spectra by equivalent electrical circuits, whose components are parametrized by the SoC, as described in U.S. Pat. No. 6,778,913, which allows development of an automotive battery tester Spectro CA-12 (Cadex Electronics Inc., Canada) based on multi-frequency electrochemical impedance spectroscopy for the acid-lead pair. The EIS spectra are approximated by equivalent electrical circuits and the evolution of the components is parametrized by the SoC. Similarly, in U.S. Pat. No. 6,037,777, the state of charge and other battery properties are determined by measuring the real and imaginary parts of the complex impedance/admittance for lead batteries or other systems. The description of the electrochemical and physical phenomena at the electrodes and in the electrolyte serving as a support for the development of the RC model, the temperature of the battery being simulated by the model, in order to increase in precision, in relation to an external measurement is described in EP 880,710.

Impedance analyses have also been described in the literature. U. Tröltzsch et al. Electrochimica Acta 51, 2006, 1664-1672. describe a method wherein they use impedance spectroscopy coupled with the adjustment of impedances according to an electrical model so as to obtain the state of health of the element. This technique however requires stopping using the element for the measurement.

French patent application 2,956,486 filed by the applicant describes a method for diagnosis of the internal state of a battery such as the SoC or the SoH using impedance measurements modelled by means of an equivalent system. A multivariate statistical analysis allows calibration of a relation between the SoC (and/or the SoH) and the parameters of the equivalent circuit characteristic of a given battery.

However, conventional diagnosis techniques using electrical measurements, such as impedance spectroscopy, remain complex techniques which are difficult to implement. Estimation of the internal state of a battery is improved if a complete diagnosis is available including state of charge and state of health, as well as the failure state of one or more elements of the battery. A non-invasive technique allowing fast diagnosis of the internal state, involving anticipation of a possible failure, of the battery is therefore required.

The acoustic emission technique allows detection of the failure of a battery even when failure cannot be detected by electric measurement. The principle of using acoustic emission to study the physical state of batteries or of components (electrodes for example) has been the subject of many academic surveys concerning notably the study of ion insertion mechanisms during charge/discharge, highlighting the sensitivity of the technique to ion insertion/disinsertion phenomena in the Li-ion battery electrode materials (for example Kalnaus, S., K. Rhodes and C. Daniel, "A study of lithium ion intercalation induced fracture of silicon particles used as anode material in Li-ion battery", Journal of Power Sources in Press, Corrected Proof (2011)), and to the phenomena of electrochemical and mechanical decrepitation of electrodes (for example Etiemble, A., H. Idrissi and L. Roue "On the decrepitation mechanism of MgNi and LaNi5-based electrodes studied by in situ acoustic emission", Journal of Power Sources 196.11 (2011): 5168-73).

However, these studies do not aim to correlate the internal state of a battery with the acoustic emission from battery elements during charge/discharge cycles.

Japanese Patent 7,006,795 describes a device allowing detection of an acoustic emission signal from a battery and to separate this signal into two signals according to their frequency so as to identify the generation of gas or the deterioration of the internal structure of the battery.

Patent application WO-11,001,471A describes a device for detecting the internal state of a battery, which can detect by acoustic emission detectors short elastic waves accompanying a reaction in a battery and which can check with precision changes in the internal state of a battery.

French patent application 2,949,908 describes a method of monitoring an electrochemical accumulator on charge or in service, which comprises a stage of direct detection of an anomaly in the accumulator, such as the progress of at least one harmful chemical reaction within the accumulator or a physical degradation of the accumulator.

However, these documents do not describe a complete method for precise diagnosis of a given internal state of a battery, including the defectiveness and/or the state of charge and of health of the battery.

Surprisingly, tests have shown that the acoustic emission technique can allow not only monitoring of the evolution of the internal state of various batteries by recording the acoustic signals produced when the batteries are operating, but also can highlight an acoustic signature of a fault or of a given internal state of the battery, through signal processing performed on the signal records. A series of comparative tests on one or more reference electrochemical systems allows defining of a relation between a given internal state and an acoustic signature which later enables fast and non-invasive diagnosis on a given electrochemical system.

The method and the system according to the invention allow determination of the internal state of a battery, notably its SoH, its state of charge SoC or its failure state, using the acoustic emission technique.

SUMMARY OF THE INVENTION

The invention relates to a method of estimating an internal state of a first electrochemical system for electrical power storage, such as a battery, wherein at least one property relative to the internal state of the first electrochemical system is estimated from an acoustic emission measurement.

The invention also relates to a system of estimating an internal state of an electrochemical system for electric power storage.

The invention furthermore relates to a smart battery management system comprising the system for estimating an internal state of the battery.

The invention also relates to a vehicle comprising a battery and a smart system of managing a battery according to the invention.

The invention also relates to a battery diagnosis system comprising a system of estimating an internal state of said battery.

The invention relates to a method of estimating an internal state of a first electrochemical system for electrical power storage, such as a battery, wherein at least one property relative to the internal state of the first electrochemical system is estimated from acoustic emission measurements, comprising the following stages:

for different internal states of at least a second electrochemical system of the same type as the first electrochemical system measuring an acoustic emission response from the second electrochemical system corresponding to each internal state, and recording for each response a signal characteristic of the acoustic emission response from the second system;

processing the recorded signals characteristic of the second system by grouping them into populations of signals having common parameters;

determining an acoustic signature of a given internal state by calibrating a relationship between at least one of the parameters common to at least one acoustic signal population and a given internal state of the second system, by an analysis of the values of one or more common parameters of the acoustic signal populations obtained for each one of said internal states;

determining an acoustic emission response from the first electrochemical system to obtain at least one signal characteristic of the acoustic emission response from the first system;

estimating the internal state of the first electrochemical system by the relationship by detecting the parameter(s) characteristic of the acoustic signature of a given internal state, in the signal characteristic of the acoustic emission response from the first system.

The method according to the invention preferably comprises:

developing a system allowing direct detection of the parameter(s) characteristic of the acoustic signature of a given internal state.

In one embodiment, the different internal states are obtained through accelerated aging of a second electrochemical system for electrical power storage of the same type as the first electrochemical system.

In another embodiment, the different internal states are obtained by selecting a set of second electrochemical systems of the same type as the first electrochemical system wherein the systems of the set have different internal states.

Preferably, at least one of the following properties relative to the internal state of the electrochemical system is calculated SoC of the system, a SoH of the system and a failure state of the system.

The acoustic signal can be defined by several parameters selected from among the following parameters: mean or maximum frequency, signal duration, signal rise time, number of counts of the signal, signal amplitude, signal energy or any combination of these parameters.

In one embodiment, the electrochemical system is in operation.

In another embodiment, the electrochemical system is at rest and an electrical signal is sent to the electrochemical system so as to put a load thereon.

The invention relates to a system of estimating an internal state of an electrochemical system for electric power storage, comprising:
  means of measuring the acoustic emission of the electrochemical system comprising a detector (G) and an acquisition system connected to the detector (G);
  a memory allowing storing of parameters of the acoustic signals characteristic of the internal state of the electrochemical system and an acoustic signature in its form of a relationship between a property relative to the internal state of the electrochemical system and the parameters of the acoustic signals characteristic of the internal state of the electrochemical system, the relationship being first calibrated by measurements for different internal states of at least a second electrochemical system of the same type as the electrochemical system;
  means for detecting parameters characteristic of the acoustic signature of a given internal state of the first electrochemical system;
  means for determining a property relative to the internal state of the electrochemical system by the relationship.

The acoustic emission measuring means preferably comprise:
  at least one (piezoelectric) detector in contact with the electrochemical system;
  an amplifier for amplifying the acoustic signal;
  an acquisition system for filtering the acoustic signals coming from the outside environment and, for recording the acoustic signals characteristic of the electrochemical system.

The acoustic emission measuring means can comprise several detectors for detecting an internal state of elements making up a battery pack or module.

The invention also relates to a smart on-board battery management system comprising a system for estimating an internal state of the battery as described above.

The invention furthermore relates to a vehicle comprising a battery and a smart on-board battery management system.

The invention also relates to a battery diagnosis system comprising a system of estimating an internal state of the battery as described above.

The diagnosis system can also comprise: a system for putting a load on the battery.

DETAILED DESCRIPTION OF THE PRESENT INVENTION

An acoustic emission is defined as a phenomenon whereby transient elastic waves are generated following local microdisplacements within a material (according to the ASTM E1316-05 standard). The term acoustic emission also designates the discipline using this phenomenon.

An acoustic emission source thus is the location of an energy dissipation through sudden variation of the stress field of a material. Upon such a variation, the energy is predominantly dissipated in form of an elastic wave, the rest being dissipated by thermal dissipation or dislocation displacement, which may in turn generate elastic waves. The waves thus created travel through the material up to the surface thereof. The signal measured by a detector located at the surface of the material is much weaker than the signal emitted at the source. It greatly depends on the nature of the emission phenomenon and on the nature of the material which is largely responsible for its attenuation. When a material undergoes a physical stress, each internal structure modification becomes a source of acoustic emission and generates transient elastic waves that propagate within the material. Detection of these signals, referred to as hits, thus allows real-time detection of the existence of these evolutions. Evaluation of the extent of these evolutions and of the nature thereof can be achieved through analysis of the acoustic parameters of the hits which are emitted. Once the stress is over, acoustic emission no longer allows the evolution undergone by the material to be detected after the event.

Many phenomena can generate acoustic emissions within a material.

The following examples can be mentioned:
  plastic deformation, dislocation movements, twinning, grain boundary sliding and Piobert-Lüders bands formation;
  inclusion or intermetallic compound rupture;
  (martensitic) phase transformation;
  crack initiation and propagation (static stress, fatigue stress, etc.);
  hydrogen embrittlement;
  localized corrosion (stress corrosion cracking, pitting, crevice);
  damage in composite materials and concrete (matrix microcracks, delamination, interface rupture, fiber rupture, etc.); and
  friction and mechanical impact.

In this (non-exhaustive) list of phenomena, there are several electrochemical processes such as metal dissolution or gaseous dihydrogen release. Thus, most electrochemical phenomena occurring simultaneously in a material making up an electrode of an electrochemical system whatever it may be (such as a battery) can be detected and identified through acoustic emission. Thus, coupled with an electrochemical measurement, the acoustic emission allows obtaining information which is complementary to the current and potential measurement which leads in particular to the discrimination of the various processes occurring on the electrode.

Instrumentation

The acoustic emission technique requires a specific instrumentation allowing the elastic waves emitted by a material to be measured. A detector is directly placed in contact with the surface of the sample being studied. A hit created by a microdisplacement first has to propagate in the material prior to reaching the surface thereof. The detector records the mechanical waves which are created and converts them into an electrical signal that is pre-amplified and then recorded by an acquisition system.

Various obstacles or natural filters clearly modify the nature and the intensity of the signals during their propagation, among which first is the material itself. The detector has to be suitably selected according to the type of source to be studied, the environmental characteristics, the sensitivity and the frequency filtering induced by the propagation in the material.

The most commonly used detectors in acoustic emission are a piezoelectric ceramic that, when in contact with the material, converts the mechanical waves into electrical signals. Proper transmission of the mechanical waves between the material and the detector is generally provided by an acoustic couplant such as a silicone grease.

At the detector outlet, the voltage levels which are generated are very low. The signal therefore has to be amplified, optionally frequency filtered (bandpass filter) and conditioned (impedance matching for signal transport, sometimes over long distances) by a pre-amplifier. The pre-amplification minimizes the perturbations induced by the surrounding medium.

The acquisition system finally allows management of the system configuration (acquisition parameters, graph type location visuals), as well as analysis through extraction of the acoustic emission characteristics when the hit is digitized. Data storage is also provided by the acquisition system.

Acoustic Emission Parameters

Acoustic emission is performed on hits and therefore occurs on a discontinuous basis. Each hit has eigenparameters that depend on the phenomena at the origin thereof. Digital acquisition of these hits allows determination of the parameters and classification of the recorded events into families each corresponding to a perturbing phenomenon within the material.

Figure 1:
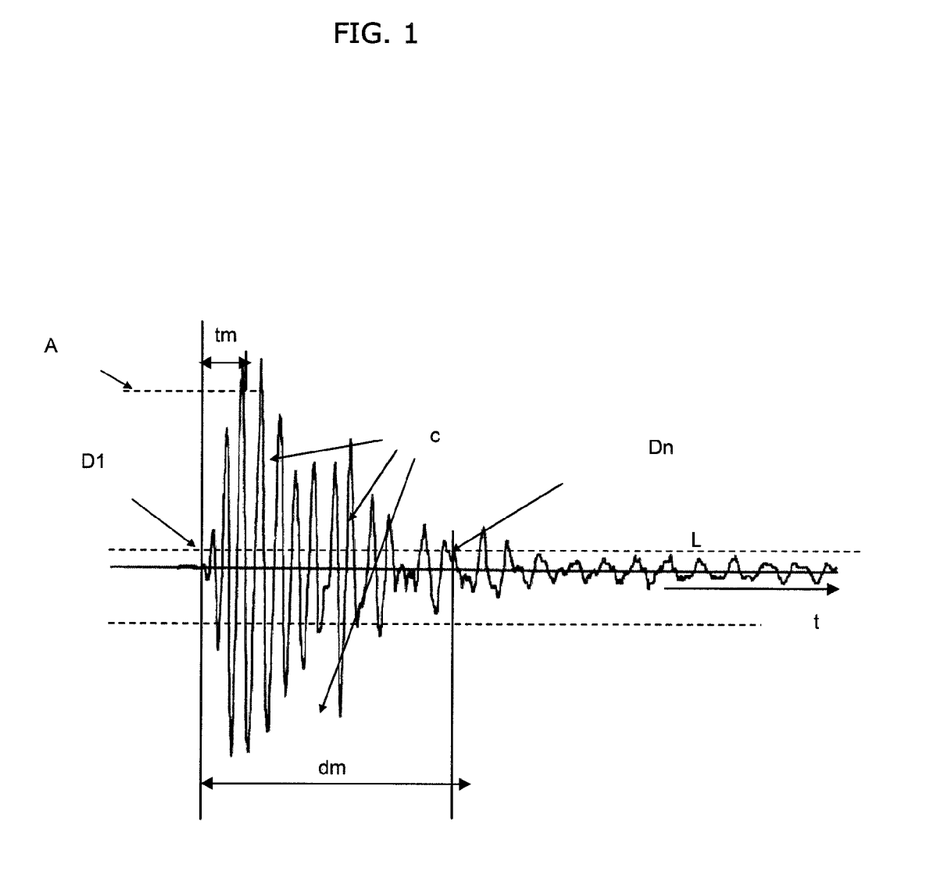
FIG. 1 shows an acoustic emission hit and the acoustic emission parameters (EA) calculated on this hit which are amplitude (A), rise time (tm), time (dm) between two threshold (L) crossings (D1 and Dn), number of pulses (c)

A typical acoustic emission hit is shown in FIG. 1 with the parameters calculated by the system.

Prior to any measurement, it is necessary to define a detection threshold (in dB) below which no hit will be measured by the detection system. The detection threshold allows defining of the start of a hit upon the first crossing thereof and thus the beginning of the calculations for the acoustic emission characteristics. It is also necessary to define temporal parameters to best perform the measurement.

The analysis parameters extracted from the digitized hits can be very numerous and they are selected by the user. A non-exhaustive and non-limitative list of parameters can be defined as follows (FIG. 1):

maximum amplitude (A in dB) which is the maximum amplitude of the signal throughout the hit;

rise time (tm in μs) which is the time interval between the first threshold crossing and the time when the maximum amplitude is reached;

duration (dm in μs) which is the time interval between the first threshold crossing ($D_1$) and the last threshold crossing ($D_n$) of the hit;

number of counts (dimensionless, c) which is the number of times the amplitude of the signal exceeds the threshold value;

energy (absolute energy or AE energy, 1 aJ=$10^{-18}$ J) which is the integral of the signal squared to duration of the hit;

peak frequency or maximum frequency ((kHz) which is the frequency at the maximum of the discrete Fourier transform of the hit; and partial power (kHz) which is the energy distribution in frequency bands. This parameter allows adjustment of the frequency bands for characterizing the spectral energy distribution of each hit. The values are given in percentage of the total energy of the hit. The energy spectral density is always calculated from a kilo point extracted from the digitized waveform.

It is then possible to carry out statistical processing of the hits by signal processing softwares. This allows discrimination of the various families of events (populations) having common parameters and thus determination of phenomena occurring within a material, as well as their duration and extent, when they are clearly identified and correlated with a family of events.

General Principle of the Method

The invention relates to a method for estimating an internal state of a first electrochemical system for electric power storage, such as a battery, wherein at least one property relative to the internal state of the first electrochemical system is estimated from an acoustic emission measurement. The method comprises the following stages:

for different internal states of at least a second electrochemical system which is the same type as the first electrochemical system measuring the acoustic emission signals corresponding to the different states of the second system in operation;

identifying among the various populations of acoustic signals at least one population directly resulting from the internal state to be estimated;

identifying at least one parameter of the acoustic signals of the at least one population distinguished from all of the other parameters of the other acoustic signals which are measured wherein the parameters of the acoustic signals are mean or maximum frequency, signal duration, signal rise time, number of counts of the signal, signal amplitude, signal energy, etc., and any other parameter or any combination of parameters which may be used to determine the acoustic signature of a given internal state; and estimating the internal state of the first electrochemical system by detecting the acoustic parameter(s) relative to the internal state of the second electrochemical system.

According to the invention, the different internal states can be obtained by varying the state of charge and/or by carrying out accelerated aging on a second electrochemical system for electrical power storage of the same type as the first electrochemical system. The different internal states can also be obtained by selecting a set of second electrochemical systems of the same type as the first electrochemical system wherein the systems of the set have different internal states.

At least one of the following properties relative to the internal state of the electrochemical system can be measured: SoC of the system, SoH of the system or a failure state of the system, insofar as one of these states generates acoustic signals with at least one parameter being distinguished from the parameters of the other acoustic signals generated by the system.

According to the invention, the electrochemical system can be in operation or stopped. In the latter case, an electrical signal is sent to the battery in order to put a load thereon. This signal can be current sent during charging of the battery or a specific electrical signal such as a current or voltage pulse.

The invention also relates to a system for estimating an internal state of an electrochemical system for electrical power storage, comprising:

- acoustic emission measuring means (G) comprising an acoustic emission detector connected to an acquisition system;
- means for calculating the parameters of the acoustic signals which are measured by the acoustic emission detector;
- a memory for storing the parameters of signals which are characteristic of the internal state of the electrochemical system; and
- means for establishing a relationship between the parameters of the calculated acoustic signals and the parameters of the internal state of the electrochemical system.

According to the invention, the acoustic emission measuring means comprise:

- a piezoelectric detector, when in contact with the electrochemical system, for detecting elastic waves propagating within the system. This detector can be for permanent or one-time contact with the electrochemical system. Contacting between the detector and the surface of the electrochemical system requires good acoustic coupling. The detector can be stuck, fixed or fastened by maintaining a pressure between the detector and the surface of the electrochemical system. Contact grease allowing suitable acoustic coupling can also be used;
- an amplifier for amplifying the acoustic signal;
- an acquisition system for filtering the acoustic signals coming from the outside environment having parameters very different from the acoustic signal generated by the electrochemical system and for recording the acoustic signals.

The invention also relates to a smart battery management system comprising a system for estimating an internal state of the battery, and a vehicle comprising a battery and a smart system of managing a battery according to the invention.

The invention also relates to any other electrical power storage system comprising a system for estimating an internal state thereof, for example a photovoltaic electrical power storage system or any other electric power storage system, notably in the field of portable electronic devices.

The invention also relates to a system comprising several detectors allowing detection of an internal state of elements making up a battery pack or module. In particular, the invention also relates to a system having detectors arranged on each element of a battery to which access to information regarding the elements is impossible to obtain (a sealed lead battery for example). In this case, the invention allows detection of the appearance of a divergence or a failure of one of the constituent elements of the pack when this divergence or failure is not detectable through global measurement of the global electrical signals of the battery pack.

The invention also relates to a system that can detect a parameter representative of a given internal state, in cases where this parameter can be detected without a signal processing stage. For example, in cases where the acoustic signature of a population is a high hit energy (higher than the energy of the other hits), a system capable of detecting the crossing of a reference hit energy threshold allows detection of the internal state of the corresponding system wherein the high energy is a sufficient acoustic signature of the state.

Flowchart of the Method

Figure 2:
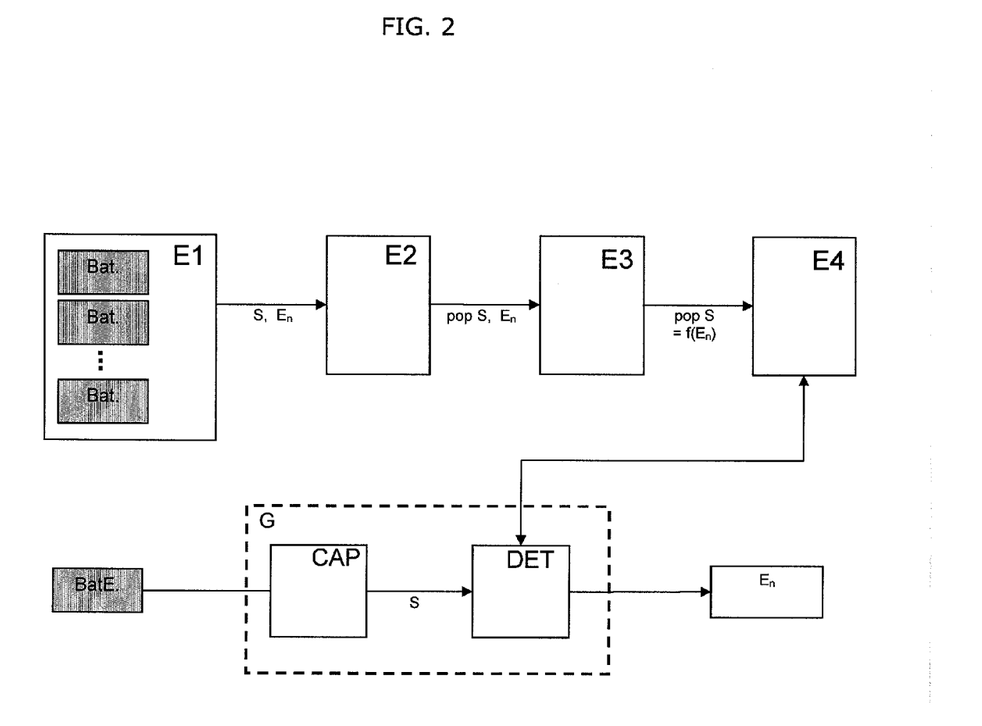
FIG. 2 shows the flowchart of the method according to the invention.

The flowchart of the method is shown in FIG. 2. The method according to the invention comprises the following stages:

Stage E1: A laboratory test campaign is conducted on a set of batteries (Bat.) in order to measure the acoustic signals produced by the batteries when a load is applied thereon (in operation, charge, discharge, current pulse, etc.) according to the SoC, the SoH, the operating state (failure or not) and the temperature in the standard operating temperature range of the batteries. Acoustic emission signals (S) corresponding to the n states (E) are obtained.

Stage E2: The recorded signals are processed by first grouping them together into populations of signals (pop S) with each population having common parameters. The parameters of the acoustic signals are of the type as follows: mean or maximum frequency, signal duration, signal rise time, number of counts of the signal, signal amplitude, signal energy, etc. Populations of signals are obtained for n states.

Stage E3: A population of events pop S is assigned to a state E of the system. For example, a population of acoustic events can be present only in a SoC range, which therefore is a sign that the battery operates in this range. A population of events can also appear from a certain aging stage and make up the acoustic signature of the battery reaching this aging stage. Finally, a population of events can appear when an irreversible degradation phenomenon leading to failure appears which constitutes the acoustic signature of the start of a battery failure.

Stage E4: Among the populations that correspond to internal states that are of interest to the user, it is desirable to identify the parameters of the signals or the combinations of parameters of the signals distinguished from the parameters of the other signals. For example, a population of events corresponding to a failure phenomenon can have a higher energy than all the other signals, or the frequency of the signals corresponding to the appearance of the full charge of an aqueous battery can be distinct from the frequencies of the other signals.

System G, which is capable of detecting on a battery (BatE) the desired internal state, is then achieved. This system includes an acoustic emission detector and an acquisition system (CAP) thereof, a device (DET) for detecting the acoustic signature of the population corresponding to the state of the desired system by identifying the characteristic parameter(s) corresponding to this population identified in stages E1 to E4.

Under load, whether during standard operation, in charge or under specific current or voltage profile conditions, battery BatE emits acoustic signals. Device G measures and processes these signals to detect the acoustic signature of the internal state(s) of the battery sends this state to the user.

Determining the Acoustic Signature Corresponding to a Given Internal State (SoC, SoH, Failure State)

A laboratory test campaign first measures the acoustic emission signals occurring on a battery according to its SoC, SoH, state of failure or not, and optionally the temperature. Generally, for different internal states of at least a second electrochemical system of the same type as the electrochemical system that is of interested to the user the property relative to the internal state of the second system (SoC, SoH, failure state) is measured; and then the acoustic emission response of this second electrochemical system is measured when load is placed thereon regarding the internal state in question.

According to one embodiment, for a given type of battery (BatE), and for a given application of this battery, a battery of the same type (Bat.) is used. Acoustic emission response measurements are then performed for different SoC, of SoH and of failure of this battery. An accelerated aging representative of the chosen application can be performed to obtain different states of health for the battery. For example, the battery is subjected, in the laboratory, to an accelerated aging protocol simulating a hybrid vehicle type on-board application or an accelerated aging protocol simulating any other application for which the power storage system is used. Aging can be prolonged until a faulty mode is obtained in particular.

The acoustic signal measurement can be obtained by applying a current or a voltage perturbation at the terminals of the battery so that the battery is not at rest (otherwise the acoustic signals are non-existent or hardly present). The acoustic signals are measured with a measuring means using an acoustic emission detector placed in contact with the battery.

Measurement of the acoustic signals according to the SoC can be done over the whole SoC range, or only in the SoC range corresponding to the range used for the application.

The evolution of the acoustic signals along with the temperature in the operating temperature range of the application is also measured.

At each SoC and/or state of aging, the acoustic signals of the electrochemical system are measured by applying a current perturbation using a galvanostat. This measurement can be conducted continuously during a complete charge or discharge of the battery.

A second battery of the same type as the first battery being studied can be used for calibration. It is also possible to use a set of batteries of the same type, with each one of the set of batteries having a different SoC and/or SoH.

Acoustic Signal Processing

A statistical processing is carried out for all of the acoustic hits which are recorded. Conventional software and signal processing methods can be used. The goal is to discriminate the different families of events having common parameters and thus to be able to correlate one or more of these families with particular internal states of the system being studied, and possibly their duration and extent, when they are clearly identified and correlated with a family of events.

When the populations of acoustic events have simple distributions, it is possible to discriminate them by representing these populations with two-dimensional axes, with the two dimensions being acoustic parameters such as, for example, the frequency of the acoustic hits as a function of their amplitude. This simple processing allows highlighting of sets of events which are grouped together into populations with close parameters.

In cases where the populations have complex distributions, a principal component analysis can be performed. Each acoustic emission signal is represented in a multidimensional space by a vector whose coordinates are the various acoustic parameters. For example, an acoustic signal can be defined by a vector of the type as follows:

$\vec{S}$=f (amplitude, energy, number of counts, duration, rise time, etc.).

Figure 3:
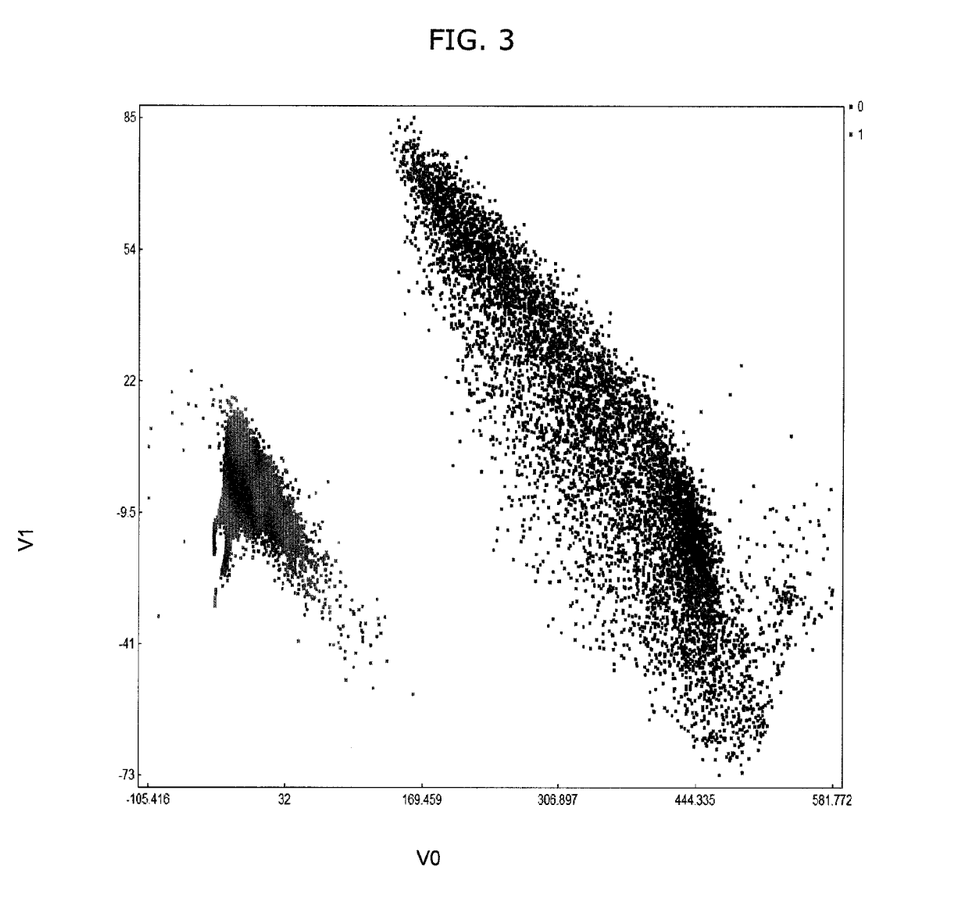
FIG. 3 shows the linear projection in a (2D) plane of acoustic data along the normed eigenvectors V0 and V1.

Dividing this set of vectors into several populations of events can then be carried out as follows:
  removing the parameters which provide no information on the physical nature of the AE signals such as the acquisition threshold and channel;
  removing the correlated parameters when the information provided by one among several parameters is sufficient;
  projection on normed eigenvectors where the normed linear projection on a (2D) plane of non-correlated parameters makes the system dimensionless and allows the dispersion of the vectors to be maximized. The dimension of the data network corresponds to the number of parameters which were projected. Thus, 2 vectors having close characteristics are represented in the same spatial region. For example, FIG. 3 shows a projection of acoustic data onto normed eigenvectors V0 and V1.

Dividing the AE signals into several classes can be obtained by a statistical processing. There are several classification methods, such as the use of a simple iterative algorithm (K-means), which tends to minimize the squared deviation between each point for a given number of populations.

When a population of events is clearly determined from the software, it can be removed from the file and statistical processing is resumed for the remaining part.

Advantages of the Method

The technique can thus constitute an alternative or complementary solution to the conventional diagnosis methods using electrical measurement such as impedance spectroscopy, which is poorly implemented due to its complexity. The interest of technique of the invention results from its non-invasive nature in view of requiring one or more detectors to be arranged and maintained at the surface of the elements of a battery pack. Diagnosis can also be very fast (in particular in case of a failure) and it can anticipate a failure (the degradation mechanisms often producing early acoustic phenomena, well before the latter influence parameters measurable through electrical measurement).

In particular, the technique allows detection of failure of a battery when the failure is not yet detectable through electrical measurement. In particular, this technique also allows detection of a defective element among several elements of a sealed battery pack for which access to information from a single element is not possible.

The resulting advantage is time and energy saving by saving recharging of a battery that is out of service. In case of reversible damage (such as lead battery desulfation for example), the method can also enable checking whether the regeneration operation has been efficient.

Applications of the Method According to the Invention

The method according to the invention allows gauging the internal state, such as the state of charge, the state of health or the failure state, of a battery previously identified for a given use, for example in a transport application (traction battery), for renewable energy storage or for any other application using electrical power storage systems. The invention strengthens the estimations achieved by the battery management system, since these data are not directly measurable.

Hybrid or Electric Vehicles

The method can be implemented on board a hybrid or electric vehicle and it allows determination of an internal state of a battery from one or more acoustic emission measurements.

Acoustic emission measurements are performed from detectors arranged directly at the surface of one or more battery elements, or indirectly via a waveguide allowing elastic waves to be transmitted. The method can be used as a complement to conventional estimation methods used by the BMS. The method can be directly integrated in the BMS.

In the automotive field, the invention can also be used for diagnosis of the batteries of electric or hybrid vehicles by the car dealer during tests. The detectors can be arranged on the battery elements by the technician carrying out the test. The detectors may also have been set during battery manufacture in anticipation of tests.

During the test, the system can be subjected to specific loads (current pulses for example) by the dealer or the test can be conducted during charging of the electric vehicle, or even online when the vehicle is in operation.

An external diagnosis kit comprises the system for estimating the internal state of batteries according to the invention. Such a kit can also comprise a system for putting a load on the battery which saves the dealer having to charge or to start the vehicle.

Battery Failure

The method according to the invention can also be used for diagnosis of the failure of one or more elements of a battery pack through the use of a multi-detector system capable of detecting acoustic signals characteristic of a degradation. Diagnosis then allows detection of the defective elements of a pack in order to change them when they are removable. It also enables detection when a pack is out of service when at least one of the elements of the pack is defective and is not removable.

Others

The internal state estimation method according to the invention can be used in any type of power storage system, notably a photovoltaic power storage system, or in the field of portable electronic devices.

The invention is advantageously applied to lead batteries, as shown in the example below.

Example : Tests Carried out on Lead Batteries

A starter lead battery having six indissociable elements was reclaimed from a dealer. This battery had already served and had low performances (charging difficulty).

Figure 4:
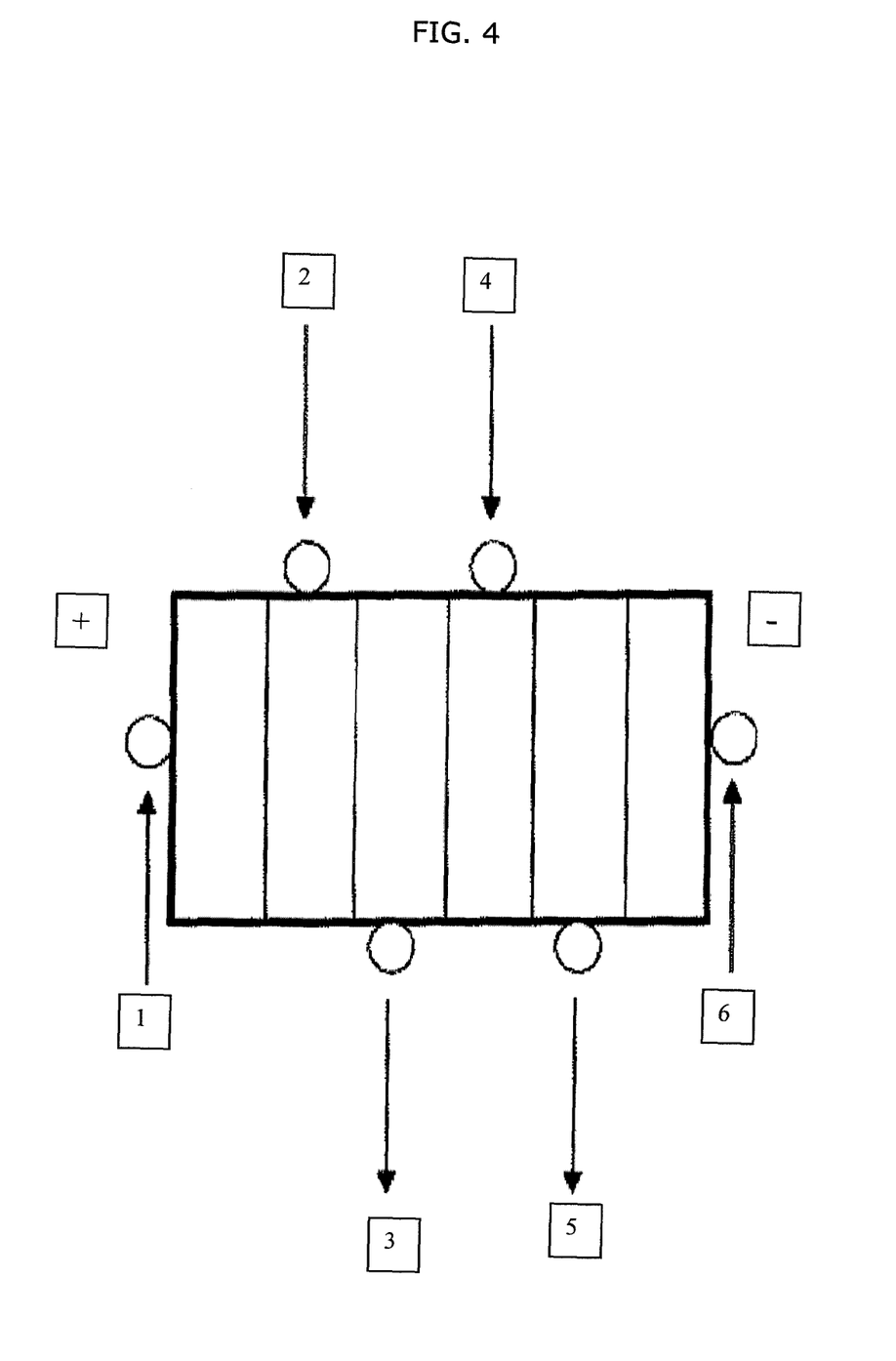
FIG. 4 shows a layout of acoustic emission detectors placed on a lead battery pack comprising 6 elements.

Six acoustic emission detectors were arranged on this battery, one per element as shown in FIG. 4.

The battery was then charged and the acoustic emission signals of each one of the six elements was recorded while charging, by the six detectors.

All of the acoustic signals recorded on each detector during charge were then processed according to analysis techniques described above. Projection of the signal vectors in certain dimensions allowed showing a population of high-energy signals on element 5, while this population of events was not present on the other elements.

Figure 5A:
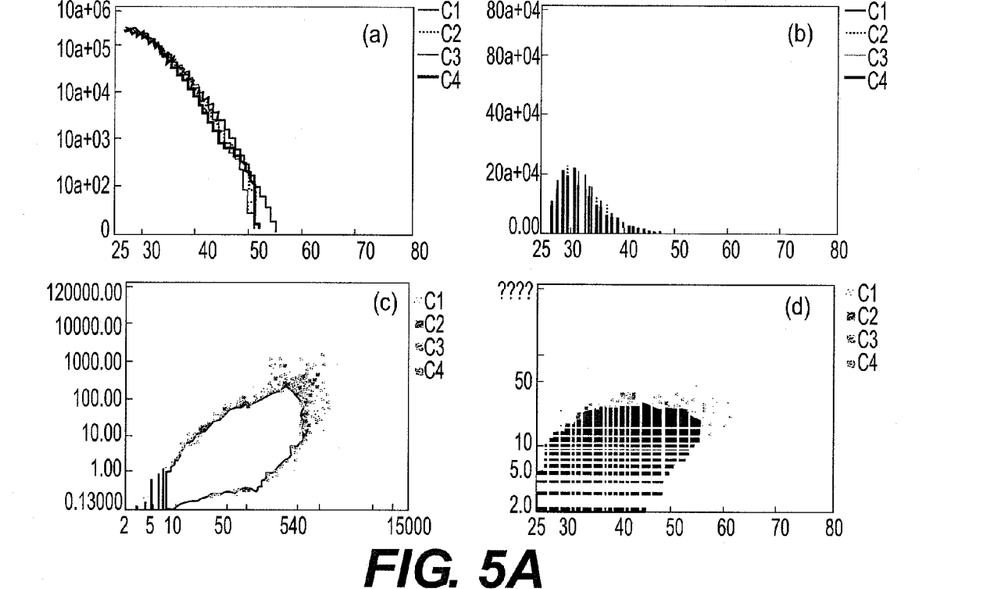
FIGS. 5A and 5B show the distributions of the acoustic signals recorded on elements 1 and 5 of a lead battery pack according to the example.
Figure 5B:
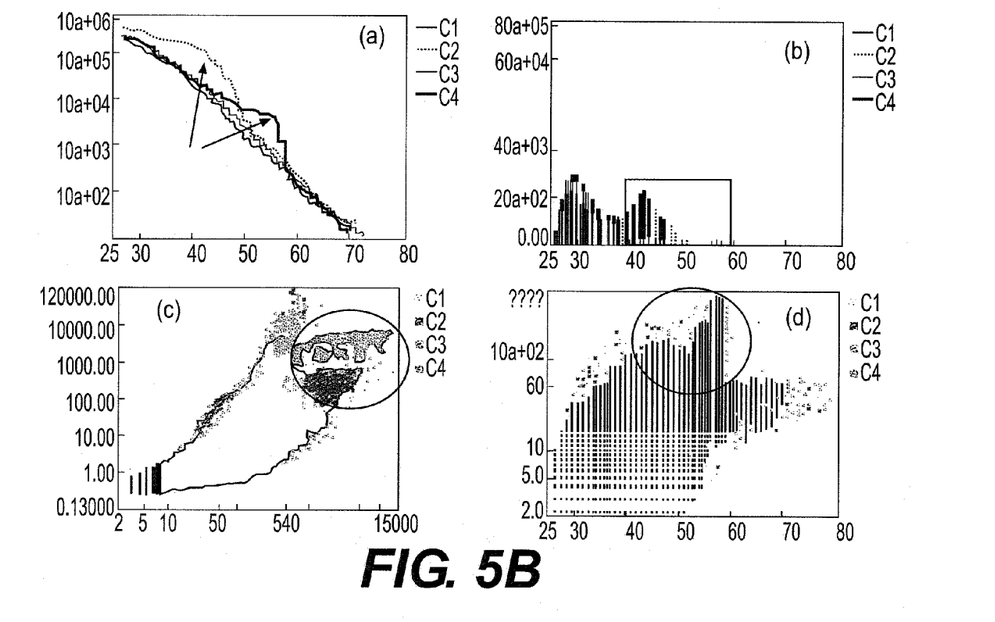

By way of example, the distributions of the signals recorded on elements 1 and 5 are shown in FIGS. 5A and 5B respectively.

FIGS. 5A (a) and 5B (a) show the distribution of the acoustic emission signals as a function of the amplitude (cumulative mode—Pollock slope).

FIGS. 5A (b) and 5B (b) show the distribution of the acoustic emission signals as a function of the amplitude.

FIGS. 5A (c) and 5B (c) show the correlation between energy and amplitude.

FIGS. 5A (d) and 5B (d) show the correlation between the number of counts and the amplitude.

The comparison between FIGS. 5A and 5B shows that element 5 highlights a population of high-energy acoustic events that does not appear on the other elements (see the signals surrounded in FIG. 5B).

Figure 6:
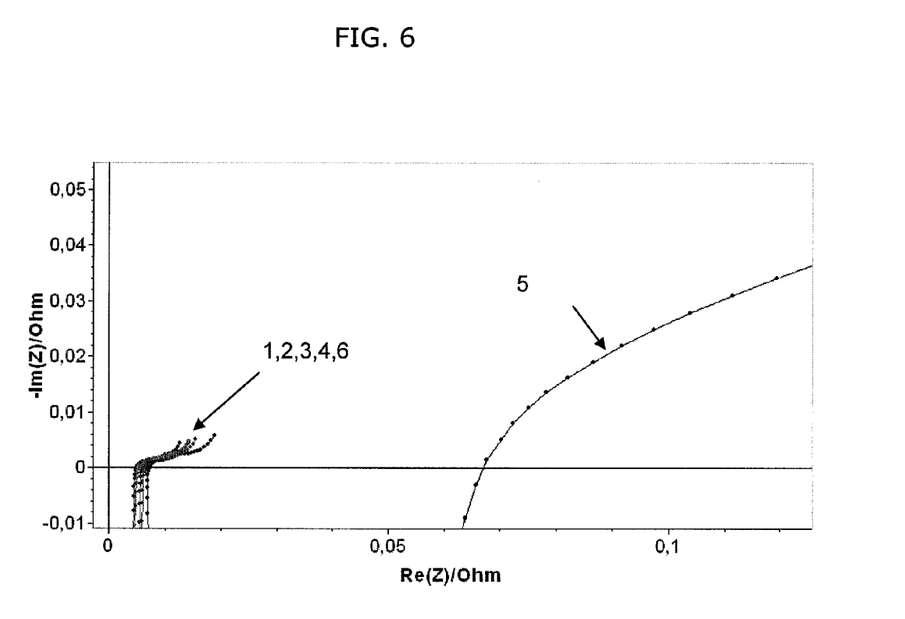
FIG. 6 shows the impedance diagrams according to the Nyquist representation of each one of the six elements of the lead battery of the example.

In order to assign this population of events to a state of the system, the battery was removed and the impedance diagram of each one of the six elements was measured using an electrochemical impedance spectroscopy technique. In high frequency (part of the diagrams intersecting the abscissa axis), the impedance measured on elements 1, 2, 3, 4 and 6 was of the order of 5 to 7 mOhms, which is a normal value (FIG. 6). The high-frequency impedance measured on element 5 was of the order of 65 mOhms, i.e. a value ten times as high, the sign of a confirmed failure of this element.

The population of high-energy acoustic events thus constitutes the acoustic signature of the failure of element 5.

By developing thereafter a detector based on the acoustic emission technique allowing identification of the population of additional events defined in FIG. 5, it is thus possible to determine the failure state of an element of a lead battery pack and therefore the failure state of the complete system, which is not reversibly removable.

The invention claimed is:

1. A method of estimating an internal state of a first electrochemical system for electrical power storage wherein at least one property relative to the internal state of the first electrochemical system is estimated from acoustic emission measurements, comprising:
    measuring for different internal states of at least a second electrochemical system of identical type as the first electrochemical system an acoustic emission response from the second electrochemical system corresponding to each internal state;
    recording for each acoustic emission response a signal characteristic of the acoustic emission response from the second system;
    processing the recorded signals characteristic of the second system by grouping the signals into populations of signals having common parameters;
    determining an acoustic signature of an internal state of the second electromechanical system by calibrating a relationship between at least one of the parameters common to at least one acoustic signal population and an internal state of the second electromechanical system by an analysis of values of at least one common parameter of the acoustic signal populations obtained for each of the internal states;
    obtaining an acoustic emission response from the first electrochemical system to obtain at least one signal characteristic of the acoustic emission measurements from the first system; and
    estimating the internal state of the first electrochemical system from the relationship by detecting at least one parameter characteristic of an acoustic signature of an internal state in the signal characteristic of the acoustic emission response from the first system.

2. A method as claimed in claim 1, comprising:
    directly detecting the at least one parameter characteristic of the acoustic signature of an internal state of the second electrochemical system.

3. A method as claimed in claim 2, wherein the different internal states of the second electrochemical system are obtained through accelerated aging of the second electrochemical system comprising an identical type as the first electrochemical system wherein the second electrochemical system is an electrical power storage.

4. A method as claimed in claim 3, wherein the different internal states of the second electrochemical system are obtained by selecting a set of second electrochemical systems of the identical type as the first electrochemical system with systems of the set having different internal states.

5. A method as claimed in claim 4, wherein at least one of SoC, SoH and failure of the state of the first electrochemical system relative to the internal state of the first electrochemical system is calculated.

6. A method as claimed in claim 3, wherein at least one of SoC, SoH and failure of the state of the first electrochemical system relative to the internal state of the first electrochemical system is calculated.

7. A method as claimed in claim 2, wherein the different internal states of the second electrochemical system are obtained by selecting a set of second electrochemical systems of the identical type as the first electrochemical system with systems of the set having different internal states.

8. A method as claimed in claim 7, wherein at least one of SoC, SoH and failure of the state of the first electrochemical system relative to the internal state of the first electrochemical system is calculated.

9. A method as claimed in claim 2, wherein at least one of SoC, SoH and failure of the state of the first electrochemical system relative to the internal state of the first electrochemical system is calculated.

10. A method as claimed in claim 2 wherein the acoustic signal is defined by parameters selected from a mean or maximum frequency, signal duration, signal rise time, a number of counts of the signal, signal amplitude, signal energy or any combination thereof.

11. A method as claimed in claim 2, comprising:
operating the first electrochemical system.

12. A method as claimed in claim 2, wherein the first electrochemical system is at rest and an electrical signal is sent to the first electrochemical system to place an electrical load thereon.

13. A method as claimed in claim 1, wherein the different internal states of the second electrochemical system are obtained through accelerated aging of the second electrochemical system comprising an identical type as the first electrochemical system wherein the second electrochemical system is an electrical power storage.

14. A method as claimed in claim 13, wherein the different internal states of the second electrochemical system are obtained by selecting a set of second electrochemical systems of the identical type as the first electrochemical system with systems of the set having different internal states.

15. A method as claimed in claim 14, wherein at least one of SoC, SoH and failure of the state of the first electrochemical system relative to the internal state of the first electrochemical system is calculated.

16. A method as claimed in claim 13, wherein at least one of SoC, SoH and failure of the state of the first electrochemical system relative to the internal state of the first electrochemical system is calculated.

17. A method as claimed in claim 13 wherein the acoustic signal is defined by parameters selected from a mean or maximum frequency, signal duration, signal rise time, a number of counts of the signal, signal amplitude, signal energy or any combination thereof.

18. A method as claimed in claim 13, comprising:
operating the first electrochemical system.

19. A method as claimed in claim 13, wherein the first electrochemical system is at rest and an electrical signal is sent to the first electrochemical system to place an electrical load thereon.

20. A method as claimed in claim 1, wherein the different internal states of the second electrochemical system are obtained by selecting a set of second electrochemical systems of the identical type as the first electrochemical system with systems of the set having different internal states.

21. A method as claimed in claim 20, wherein at least one of SoC, SoH and failure of the state of the first electrochemical system relative to the internal state of the first electrochemical system is calculated.

22. A method as claimed in claim 20 wherein the acoustic signal is defined by parameters selected from a mean or maximum frequency, signal duration, signal rise time, a number of counts of the signal, signal amplitude, signal energy or any combination thereof.

23. A method as claimed in claim 20, comprising:
operating the first electrochemical system.

24. A method as claimed in claim 20, wherein the first electrochemical system is at rest and an electrical signal is sent to the first electrochemical system to place an electrical load thereon.

25. A method as claimed in claim 1, wherein at least one of SoC, SoH and failure of the state of the first electrochemical system relative to the internal state of the first electrochemical system is calculated.

26. A method as claimed in claim 25 wherein the acoustic signal is defined by parameters selected from a mean or maximum frequency, signal duration, signal rise time, a number of counts of the signal, signal amplitude, signal energy or any combination thereof.

27. A method as claimed in claim 25, comprising:
operating the first electrochemical system.

28. A method as claimed in claim 25, wherein the first electrochemical system is at rest and an electrical signal is sent to the first electrochemical system to place an electrical load thereon.

29. A method as claimed in claim 1 wherein the acoustic signal is defined by parameters selected from a mean or maximum frequency, signal duration, signal rise time, a number of counts of the signal, signal amplitude, signal energy or any combination thereof.

30. A method as claimed in claim 29, comprising:
operating the first electrochemical system.

31. A method as claimed in claim 29, wherein the first electrochemical system is at rest and an electrical signal is sent to the first electrochemical system to place an electrical load thereon.

32. A method as claimed in claim 1, comprising:
operating the first electrochemical system.

33. A method as claimed in claim 1, wherein the first electrochemical system is at rest and an electrical signal is sent to the first electrochemical system to place an electrical load thereon.

34. A system for estimating an internal state of a first electrochemical system for electrical power storage, comprising:
a detector for measuring an acoustic emission of acoustic signals emitted from the first electrochemical system;
an acquisition system coupled to the detector;
a memory for storing parameters of acoustic signals characteristic of an internal state of the first electrochemical system and an acoustic signature as a relationship between a property relative to the internal state of the first electrochemical system and the parameters of the acoustic signals characteristic of the internal state of the first electrochemical system where the relationship is first calibrated by measurements of different internal states of at least a second electrochemical system of an identical type as the first electrochemical system;
means for detecting parameters characteristic of an acoustic signature of an internal state of the first electrochemical system; and
means for determining a property relative to the internal state of the first electrochemical system by using the relationship.

35. A system as claimed in claim 34, wherein the detector comprises:
at least one piezoelectric detector in contact with the first electrochemical system;

an amplifier for amplifying the acoustic signals; and
a system for filtering the acoustic signal from an environment outside the first electrochemical system and for recording the acoustic signals emitted from the first electrochemical system.

36. A system as claimed in claim 35 comprising:
detectors for detecting an internal state of elements of a battery pack or module.

37. A system according to claim 34 comprising:
an onboard battery management system for estimating an internal state of the first electrochemical system comprising a battery.

38. A system according to claim 37 comprising a vehicle.

39. A system according to claim 34 comprising a battery diagnosis system for estimating an internal state of the first electrochemical system comprising a battery.

* * * * *